United States Patent [19]

Orito et al.

[11] 4,329,487
[45] May 11, 1982

[54] METHOD FOR THE ASYMMETRIC HYDROGENATION OF α-KETOESTERS

[75] Inventors: Yoshio Orito, Musashino; Sumi Imai, Funabashi; Shuichi Niwa, Yatabe, all of Japan

[73] Assignee: Director-General of Agency of Industrial Science and Technology, Tokyo, Japan

[21] Appl. No.: 124,149

[22] Filed: Feb. 25, 1980

[30] Foreign Application Priority Data

Jun. 5, 1979 [JP] Japan .................................. 54/70234

[51] Int. Cl.³ ...................... C07C 69/76; C07C 69/66; B01J 31/02
[52] U.S. Cl. ...................................... 560/60; 252/430; 252/429 R; 560/179
[58] Field of Search .................. 560/60, 179; 252/430, 252/429 R

[56] References Cited

U.S. PATENT DOCUMENTS

| | | | |
|---|---|---|---|
| 2,278,549 | 4/1942 | Loden | 560/60 |
| 2,797,233 | 6/1957 | Lott | 560/60 |
| 3,663,597 | 5/1972 | Flitter | 560/60 |
| 3,852,323 | 12/1974 | Diamond et al. | 560/60 |

FOREIGN PATENT DOCUMENTS

| | | | |
|---|---|---|---|
| 2409761 | 11/1975 | Fed. Rep. of Germany | 560/60 |
| 1015805 | 1/1966 | United Kingdom | 252/430 |
| 1200233 | 7/1970 | United Kingdom | 252/430 |
| 1355682 | 6/1974 | United Kingdom | 560/60 |

*Primary Examiner*—Paul J. Killos
*Attorney, Agent, or Firm*—Birch, Stewart, Kolasch and Birch

[57] ABSTRACT

A method for the asymmetric hydrogenation of α-ketoesters which comprises subjecting an α-ketoester containing an α-ketoester grouping of the formula: —CO—COO— to assymmetric hydrogenation in the presence of a platinum-alumina catalyst modified with a solution of a cinchona-alkaloid.

5 Claims, No Drawings

METHOD FOR THE ASYMMETRIC HYDROGENATION OF α-KETOESTERS

BACKGROUND OF THE INVENTION

This invention relates to a method for the asymmetric hydrogenation of α-ketoesters in the presence of a specific catalyst.

A variety of studies have been made heretofore on the methods for the asymmetric hydrogenation of α-ketoesters. For example, there are known a method wherein a benzoylformate or a pyruvate is reacted with hydrosilane in the presence of a rhodium complex containing an optically active ligand and then the reaction product is decomposed and a method wherein an optically active 1,4-dihydronicotinamide derivative as the so-called NADH model compound, i.e. a typical coenzyme of an enzyme for biochemical reduction reactions, is reacted in the presence of magnesium perchlorate with methyl benzoylformate to obtain an optically active mandelate in an extremely high yield of the asymmetric product.

However, the methods for the asymmetric hydrogenation of α-ketoesters proposed heretofore have such drawbacks that a catalyst used therein is liquid and is thus difficult to separate itself from the reaction product and that the preparation of such catalyst is difficult. If it is possible to use a solid catalyst for these methods, the above described drawbacks will be overcome. However, a solid catalyst exhibiting a high rate of asymmetric hydrogenation has not yet been developed.

BRIEF SUMMARY OF THE INVENTION

It is, therefore, a prime object of this invention to provide a method for the asymmetric hydrogenation of α-ketoesters in the presence of a solid catalyst.

It is another object of this invention to provide a solid catalyst which exhibits a high rate of asymmetric hydrogenation for α-ketoesters.

Other objects, features and advantages of this invention will become apparent from the detailed description which follows.

DETAILED DESCRIPTION OF THE INVENTION

As a result of extensive research made for developing a solid catalyst which exhibits a high rate of asymmetric hydrogenation for α-ketoesters, it has now been found that a platinum-alumina catalyst modified with a solution of a cinchona-alkaloid is suitable for this purpose. This invention has been accomplished on the basis of the above finding.

In accordance with this invention, there is provided a method for the asymmetric hydrogenation of α-ketoesters containing an α-ketoester grouping —CO—COO— in the presence of a solid catalyst, characterized in that a platinum-alumina catalyst modified with a solution of a cinchona-alkaloid is used as the solid catalyst.

In the present invention, the platinum-alumina catalyst modified with a solution of a cinchona-alkaloid is prepared by immersing a usual platinum-alumina catalyst into a solution of a cinchona-alkaloid in an organic solvent whereby the cinchona-alkaloid is sufficiently adsorbed on the platinum-alumina catalyst. Usually, the amount of cinchona-alkaloid adsorbed on the platinum-alumina catalyst is in sufficient excess of the saturated adsorption amount. A solution of the cinchona-alkaloid has a concentration of 0.1–10%, preferably 0.5–3% and is used preferably in a volume of 20–100 ml per 0.5 g of the platinum-alumina catalyst. Any of the organic solvents capable of dissolving a cinchona-alkaloid, such as ethanol, propanol and tetrahydrofuran can be used in this invention. The platinum-alumina catalyst is immersed in a solution of the cinchona-alkaloid for a period of several hours or longer at a temperature ranging from room temperature to reflux temperature.

Various kinds of cinchona-alkaloids can be used in this invention, but the use of quinine(−), quinidine(+), cinchonine(+) and/or cinchonidine(−) is advantageous because of their easy availability. The reason why the platinum-alumina catalyst modified with a cinchona-alkaloid exhibits a high rate of selectivity to asymmetry in this invention is still unknown. However, it is supposed to be ascribable to the reason that since a cinchona-alkaloid has in its molecule two nitrogen atoms and an asymmetric carbon atom carrying one hydroxyl group, this compound is adsorbed on the platinum atom and on the other hand influences the configuration of the adsorbed reactant.

The platinum-alumina catalyst used in this invention may be a commercially available powdery material which, when well dried, gives a fairly high yield of asymmetric products. However, a better result can be obtained when such catalyst is preheated in a stream of hydrogen prior to the modification with a cinchona-alkaloid. The temperature for preheating the catalyst is preferably within the range of 250°–500° C. The content of platinum in the catalyst is about 0.5–20%, preferably 1–10% by weight.

The method of this invention is preferably carried out by immersing the platinum-alumina catalyst into a solution of the cinchona-alkaloid to modify the catalyst therewith, removing the supernatant liquid from the catalyst, charging the resultant modified catalyst together with the reactant (α-ketoester), a reaction solvent and, if necessary, a reaction additive (for example, an organic amine) into a pressure container such as an autoclave and hydrogenating the reactant under pressurized hydrogen. This hydrogenation reaction proceeds at room temperature and is completed after adsorption of an almost theoretical amount of hydrogen. After completion of the reaction, the catalyst used is filtered off and the reaction liquid is distilled to remove the solvent. The distillation residue is then subjected to distillation under reduced pressure to separate the end product. The optical yield of the resultant ester varies, as will be evident from Examples, according to the reaction conditions adopted but is as high as 55–86% to which the yields of the conventional methods have not yet reached.

The hydrogenation reaction is carried out in a pressure container such as an autoclave. The hydrogen pressure applied is 2–100 atm. The reaction proceeds at room temperature. If necessary, the reaction mixture may be heated up to the boiling temperature of a solvent used. Alcohols, ethers, esters and aromatic hydrocarbons such as benzene are used as solvents for this reaction. The yield of the asymmetric product is increased by adding a small amount of an amine or the same cinchona-alkaloid as used for the modification of the catalyst, to the reaction solvent.

The method of this invention for asymmetric hydrogenation is applied to various α-ketoesters having an α-ketoester grouping —CO—COO—, irrespective of whether they are aromatic or aliphatic. Illustrative of such α-ketoesters are, for example, esters of pyruvic acid ($CH_3COCOOH$), benzoylformic acid ($C_6H_5COCOOH$) and phenylpyruvic acid ($C_6H_5COCH_2COCOOH$) with various alcohols. Examples of the alcohol used for this purpose include $C_1$-$C_8$ lower alcohols such as ethanol, propanol, butanol, hexanol and octanol. The α-ketoester grouping —CO—COO— contained in the starting ester compound is converted according to the method of this invention into an asymmetrically hydrogenated hydroxyester grouping —CH(OH)—COO—. The optically active hydroxyesters obtained according to the method of this invention are useful as starting materials for medicaments.

This invention will now be illustrated in more detail by way of Examples wherein percentage is shown by weight unless otherwise indicated.

EXAMPLE 1

In a quartz tube was placed 0.5 g of a 5% platinum-alumina catalyst. The catalyst was maintained for 2 hours at 400° C. in a stream of hydrogen. The catalyst thus preheated was added to 40 ml of an ethanolic solution of cinchonidine and allowed to stand stationarily in the solution for 20 hours at room temperature. The ethanolic solution of cinchonidine was then removed from the catalyst by the aid of a centrifugal sedimenter. A 100 ml autoclave was charged with the catalyst treated above, 10 ml of methyl benzoylformate and 30 ml of methyl propionate. The hydrogenation reaction was carried out at room temperature with hydrogen under an initial pressure of 60 kg/cm². The reaction was ceased when an almost theoretical amount of hydrogen was absorbed. After completion of the reaction, the catalyst was filtered off and the reaction liquid was subjected to distillation whereby methyl propionate was first removed and then 10.7 g of methyl mandelate was distilled at 115°-116° C./7 mmHg. The later ester had a specific rotation $[\alpha]_D^{25}$ of $-100.8°$ (ethanol). As optically pure methyl (−)-mandelate has a specific rotation $[\alpha]_D^{25}$ of $-134.0°$ (ethanol), the yield of the asymmetric product was 75.2%.

EXAMPLE 2

In the same manner as described in Example 1, 0.5 g of a 5% platinum-alumina catalyst was preheated in a stream of hydrogen and then modified with a 1% ethanolic solution of cinchonidine.

An autoclave having a capacity of 100 ml was charged with the catalyst treated above, 10 ml of ethyl benzoylformate and 30 ml of ethyl ether and the hydrogenation reaction was carried out at room temperature with hydrogen under an initial pressure of 50 kg/cm². After completion of the reaction, the catalyst was filtered off and the reaction liquid was subjected to distillation whereby ethyl ether was removed first and then 10.2 g of ethyl mandelate was distilled at 121°-122° C./6 mmHg. The resultant ester had a specific rotation $[\alpha]_D^{20}$ of $-107.8°$ (chloroform). As optically pure ethyl (−)-mandelate has a specific rotation $[\alpha]_D^{20}$ of $-128.4°$ (chloroform), the yield of the asymmetric product was 83.9%.

EXAMPLE 3

In a quartz tube, 0.5 g of a 5% platinum-alumina catalyst was placed and heated for 2 hours at 350° C. in a stream of hydrogen. The preheated catalyst was immersed into 40 ml of a 1% ethanolic solution of cinchonidine and the mixture was heated for 4 hours under reflux on a water bath. The ethanolic solution of cinchonidine was then removed from the catalyst by the aid of a centrifugal sedimenter. A 100 ml autoclave was charged with the catalyst thus treated, 12 ml of methyl pyruvate, 24 ml of ethanol and 0.1 g of cinchonidine. The hydrogenation reaction was carried out at room temperature with hydrogen under an initial pressure of 70 kg/cm². After completion of the reaction, the catalyst was filtered off and the reaction liquid was subjected to distillation whereby ethanol was removed first and 11.2 g of methyl lactate was then distilled at 66°-67° C./40 mmHg. This ester had a specific rotation $[\alpha]_D^{20}$ of 6.79°. As optically pure methyl (+)-lactate has a specific rotation $[\alpha]_D^{20}$ of +8.25, the yield of the asymmetric product was 82.3%.

EXAMPLE 4

0.5 Gram of a 5% platinum-alumina catalyst was maintained for 2 hours at 400° C. in a stream of hydrogen, and then immersed into 40 ml of a 1% ethanolic solution of cinchonidine for 20 hours at room temperature. A 100 ml autoclave was charged with the catalyst thus treated, 12 ml of methyl pyruvate and 24 ml of benzene and the hydrogenation reaction was carried out with hydrogen under an initial pressure of 70 kg/cm². After completion of the reaction, the catalyst was filtered off and the reaction liquid was subjected to distillation whereby the benzene was first removed and then 11.8 g of methyl lactate was distilled at 66°-67° C./40 mmHg. The ester had a specific rotation $[\alpha]_D^{20}$ of +6.66°. The yield of the asymmetric product was 80.8%.

Except that at the time of charging the autoclave with the above mentioned catalyst, reactant and solvent 0.2 g of triethylamine was added to the mixture, the operation was conducted in the same manner as described above whereby 11.6 g of methyl lactate was obtained which had a specific rotation $[\alpha]_D^{20}$ of +7.03°. The yield of the asymmetric product was thus increased to 85.2%.

EXAMPLE 5

0.5 Gram of a 5% platinum-alumina catalyst was preheated for 2 hours at 400° C. in a stream of hydrogen and then immersed into a 1% ethanolic solution of quinine for 20 hours at room temperature. A 100 ml autoclave was charged with the catalyst thus treated, 12 ml of methyl pyruvate, 24 ml of benzene and 0.1 g of quinine and the hydrogenation reaction was carried out at room temperature with hydrogen under an initial pressure of 70 kg/cm². After completion of the reaction, the catalyst was filtered off and the reaction liquid was subjected to distillation whereby benzene was first removed and then 11.8 g of methyl lactate was distilled at 66°-67° C./40 mmHg. This ester had a specific rotation $[\alpha]_D^{20}$ of +7.16. The yield of the asymmetric product was 86.8%.

Except that a 1% ethanolic solution of quinidine was used as the modifying liquid and 0.1 g of quinidine was used in place of the quinine as additive to the reaction liquid, the operation was conducted in the same manner as described above whereby 11.0 g of methyl lactate was obtained which had a specific rotation $[\alpha]_D^{20}$ of −4.59°. The yield of the asymmetric product was 55.6%.

EXAMPLE 6

0.5 Gram of a 5% platinum-alumina catalyst was preheated for 2 hours at 400° C. in a stream of hydrogen and then immersed into a 1% aqueous tetrahydrofuran solution of cinchonine for 20 hours at room temperature. A 100 ml autoclave was charged with the catalyst thus treated, 12 ml of methyl pyruvate, 24 ml of benzene and 0.1 g of cinchonine and the hydrogenation reaction was carried out under the same conditions as those described in Example 5 whereby 11.4 g of methyl lactate was obtained which had a specific rotation $[\alpha]_D^{20}$ of $-6.17°$. The yield of the asymmetric product was 74.8%.

EXAMPLE 7

0.5 Gram of a 5% platinum-alumina catalyst was preheated for 2 hours at 450° C. and then immersed into a 1% ethanolic solution of quinine for 20 hours at room temperature. A 100 ml autoclave was charged with the catalyst thus treated, 12 ml of ethyl pyruvate, 24 ml of benzene and 0.1 g of quinine and the hydrogenation reaction was carried out at room temperature with hydrogen under an initial pressure of 70 kg/cm². After completion of the reaction, the catalyst was removed by filtration and the reaction liquid was subjected to distillation whereby the benzene was first removed and then 11.3 g of ethyl lactate was distilled at 68°–69° C./33 mmHg. This ester had a specific rotation $[\alpha]_D^{20}$ of $+9.45°$. As optically pure ethyl lactate has a specific rotation $[\alpha]_D^{20}$ of $+12°$, the yield of the asymmetric product was 78.8%.

As many apparently widely different embodiments of this invention may be made without departing from the spirit and scope thereof, it is to be construed that this invention is not limited to the specific embodiments illustrated in the examples except as defined in the appended claims.

What is claimed is:

1. A method for the asymmetric hydrogenation of α-ketoesters containing an α-ketoester grouping of the formulae —CO—COO—, which comprises subjecting an α-ketoester of an α-keto acid selected from pyruvic acid and benzoylformic acid to asymmetric hydrogenation in the presence of an platinum-alumina catalyst modified with a solution of a cinchona-alkaloid.

2. A method according to claim 1 wherein said cinchona-alkaloid is selected from at least one member of the group consisting of quinine (−), quinidine (+), cinchonidine (−) and cinchonine (+).

3. A catalyst for the asymmetric hydrogenation of α-ketoesters containing an α-ketoester grouping of —CO—COO—, said α-ketoester comprising an ester of an α-ketoacid selected from pyruvic acid and benzoylformic acid which comprises a platinum-alumina catalyst modified with a solution of cinchona-alkaloid.

4. A catalyst according to claim 3, wherein the platinum content is 0.5–10% by weight.

5. A catalyst according to claim 3, wherein the cinchona-alkaloid is selected from at least one member of the group consisting of quinine (−), quinidine (+), cinchonidine (−) and cinchonine (+).

* * * * *